United States Patent [19]

Oakley

[11] Patent Number: 4,772,282

[45] Date of Patent: Sep. 20, 1988

[54] DRAW-STRING ABSORBENT DEVICE INCLUDING MEANS FOR PACKAGING AND DISPOSAL

[75] Inventor: Barbara A. Oakley, Menasha, Wis.

[73] Assignee: Kimberly-Clark Corporation, Neenah, Wis.

[21] Appl. No.: 925,338

[22] Filed: Oct. 31, 1986

[51] Int. Cl.⁴ ............................................. A61F 13/16
[52] U.S. Cl. ................................ 604/385.1; 604/386
[58] Field of Search ................. 604/385.1, 385.2, 386, 604/387

[56] References Cited

U.S. PATENT DOCUMENTS 1,329,119  1/1920  George .......................... 604/385.1
3,575,172  4/1971  Kiela ............................. 604/385.1
4,182,336  1/1980  Black ............................. 604/387

Primary Examiner—John D. Yasko
Attorney, Agent, or Firm—Paul A. Leipold

[57] ABSTRACT

The invention is generally accomplished by providing a feminine pad having flap areas extending outside of the longitudinal sides of the absorbent pad. The longitudinal flaps are provided with channels containing strings. Prior to use and for disposal after use, the pad may be rolled and the strings tightened to hold the rolled pad in a roll, as well as close and protect the sides of the rolled pad. In a preferred embodiment, the strings may be provided that are shorter than the pad in order to shorten the edges of the flap to shape the pad and provide liquid barriers at the pad edge to minimize leakage of the pad when in use.

18 Claims, 5 Drawing Sheets

DRAW-STRING ABSORBENT DEVICE INCLUDING MEANS FOR PACKAGING AND DISPOSAL

TECHNICAL FIELD

The subject invention relates to incontinent garments and sanitary napkins and particularly to a sanitary napkin having draw strings in the edges to aid in its packaging and disposal.

BACKGROUND ART

One of the problems associated with the use of sanitary napkins has been their disposal. Used napkins are unattractive and can be messy. Attempts to provide disposal aids have generally followed one of several directions. The first of these involves the use of a bag or bag-like attachment affixed to or a part of a sanitary napkin. Examples of various embodiments of this approach can be found in U.S. Pat. No. 4,182,336—Black, 3,604,423—Fraser and 3,274,999—Robinson.

The self-contained bag has been unsuccessful for a variety of reasons. The self-contained bag is on the bottom of the napkin and therefore must, by its nature interfere with adhesive attachment of the napkin to the panty. Also, a napkin with such a self-contained bag is both expensive and difficult to manufacture.

Another alternative involves the utilization of adhesive areas at the longitudinal ends of the garment facing side of the napkin. These adhesive areas may be covered by an extension or an added element and after the napkin is used, it is rolled into a tightly wound cylinder with the adhesive tab being used to fasten the roll. This approach, while simpler from a manufacturing standpoint, still involves the use of a separate tab and the user of the napkin must touch the soiled napkin to be able to roll it. Also, extremely thick napkins are difficult to roll because of limited flexibility. The pressure involved in rolling a napkin can, in certain instance, provide for fluid "strikeback" through the wrapper of the napkin. For this reason a disposal system of the type disclosed in U.S. Pat. No. 3,626,945—Mobley has met with little success.

U.S. Pat. Nos. 2,742,903—Lightner and 4,072,151—Levine have a structure which places adhesive on the body-facing side of the sanitary napkin for direct attachment to the wearer.

Another alternative disclosed in U.S. Pat. No. 4,402,689—Baum —is a sanitary napkin having an absorbent layer wrapped with a fluid permeable wrap and provided with a baffle approximately twice the width of the conventional baffle. The baffle is attached to the bottom of the outside portion of the wrap so that the baffle is fully exposed. The baffle is also folded over onto itself. The fold is maintained in place by positioning means such as an adhesive area and the garment facing side of the folded baffle is provided with garment suspension adhesive or other attachment means. After the napkin is used the baffle is unfolded with the free flap positioned over the top portion of the napkin and attached by adhesive or other means to either the wrap or the opposite side of the baffle. The used portion of the napkin is at least partially visually screened and the napkin can be readily disposed of without the user having to touch the soiled napkin surface.

It has been proposed that disposable diapers be provided with draw strings. In U.K. Patent Application 2,001,236—Pigneul—a diaper is provided with adjustable strings which allow tightening of the crotch area after the diaper is placed on the infant.

U.S. Pat. No. 4,034,760—Amirsakis—discloses a disposable diaper that may be turned inside out to form a bag for the used diaper. The bag may be provided with a draw string to pull the bag around the diaper.

U.S. Pat. No. 3,024,788—Lane—discloses a catamenial device that is provided with an integral bag that may be used in disposal of the device. The bag further has a draw string to close it after covering the sanitary napkin.

THE INVENTION

The object of this invention is to overcome disadvantages of prior pads for absorption of human exudate.

Another object of the instant invention is to provide a feminine pad with convenient disposal means.

A further object of the invention is to provide an incontinent or feminine pad that is convenient to carry prior to use.

These and other objects of the invention are generally accomplished by providing a feminine pad having flap areas extending outside of the longitudinal sides of the absorbent pad. The longitudinal flaps are provided with channels containing strings. Prior to use and for disposal after use, the pad may be rolled and the strings tightened to hold the rolled pad in a roll, as well as close and protect the sides of the rolled pad. In a preferred embodiment, the strings may be provided that are shorter than the pad in order to shorten the edges of the flap to shape the pad into a curve and provide upward extending barriers at the pad edge to minimize leakage of the pad when in use.

MODES FOR CARRYING OUT THE INVENTION

The pad for absorption of human exudate and the backing member of the invention provide numerous advantages over prior pads. The pads of the invention, having primary use as feminine care or incontinence pads, have numerous advantages over prior structures. The pads of the invention with adjustment strings provide a means of packaging the pad prior to use and also provide a means for conveniently and discreetly rolling and disposing of the pad after use. The system of the invention further provides a shaped pad without the use of elastic or expensive molded foam materials. The system of the invention provides a pad that is easy to form as the general design is rectangular without use of exotic materials or the difficulties of elastic application. These and other advantages of the invention will be apparent in view of the detailed description that follows.

Figure 1:
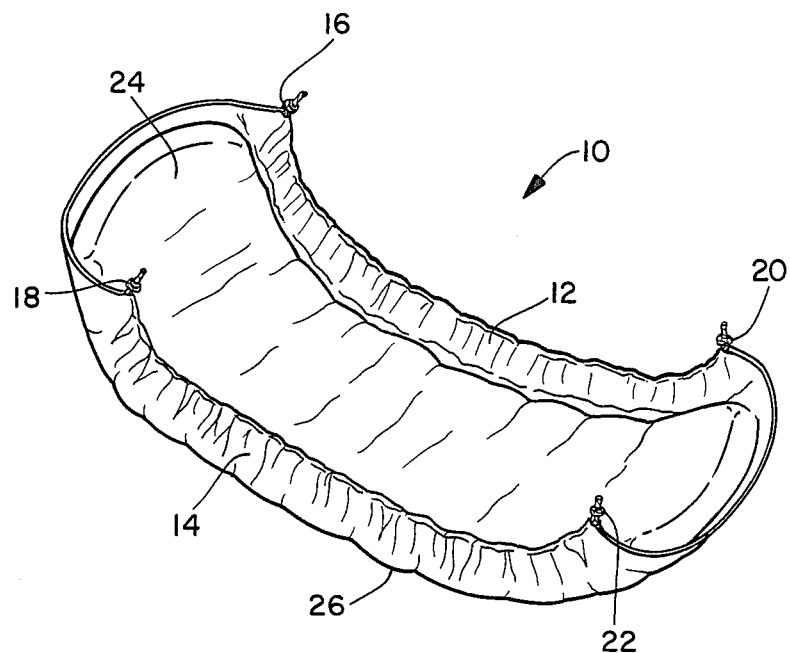
FIG. 1 is a perspective view of a pad in accordance with the invention.

FIG. 1 is a perspective view of a pad 10 in accordance with the invention. The pad is provided with upstanding sides 12 and 14. In the upper edges of the sides are draw strings terminating in exposed ends 16, 18, 20 and 22. The absorbent pad portion 24 lies in the bottom of the trough formed by the upstanding sides 12 and 14. The backing member 26 is impervious so that fluids will not penetrate out of the trough formed by sides 12 and 14.

Figure 2:
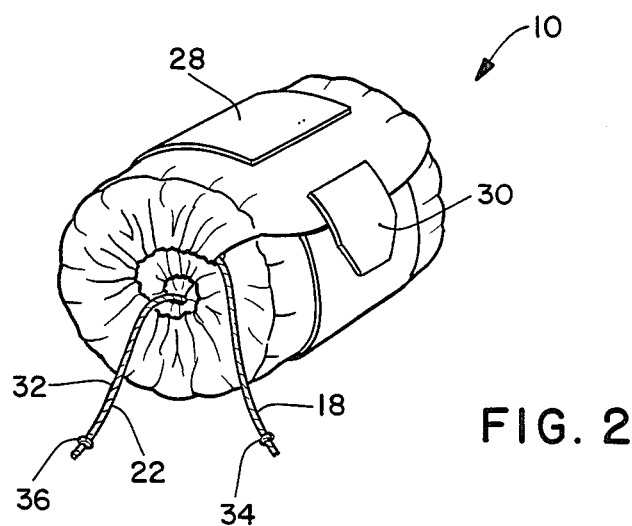
FIG. 2 is a perspective view of a pad of the invention rolled prior to use.

FIG. 2 is a perspective view of the pad 10 as it would be presented for sale to the user. The pad is provided with a peel strip 28 that is removed to expose the garment attachment adhesive not shown. Sealing strip 30 may be broken or removed to unwrap the pad. The ends 18 and 22 of string 32 have been pulled to tighten the side flap 14 around the end of the rolled pad 10 to prevent contamination of the pad. String 32 terminates in knots 34 and 36.

Figure 5:
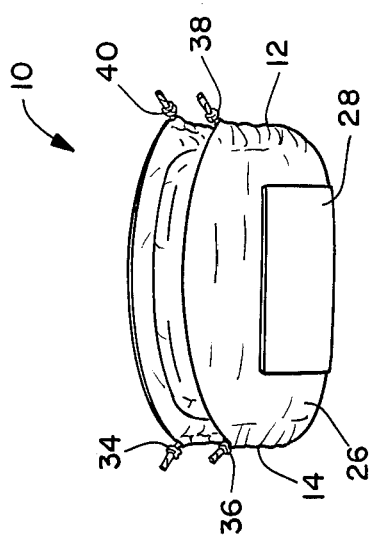
FIG. 5 is an end view of the pad of the invention.
Figure 6:
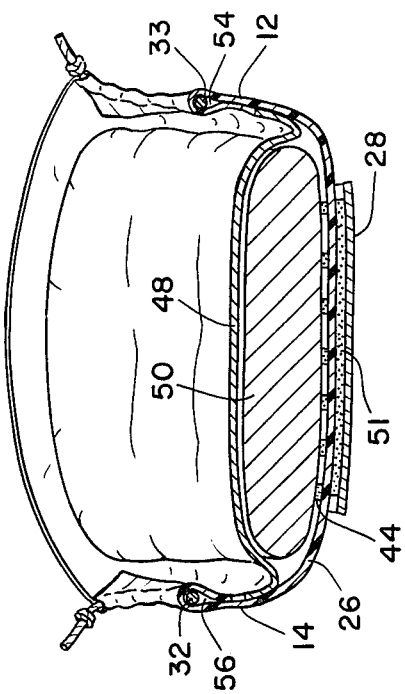
FIG. 6 is a cross-sectional view of the pad of FIG. 3 on cross-sectional line 6—6.
Figure 4:
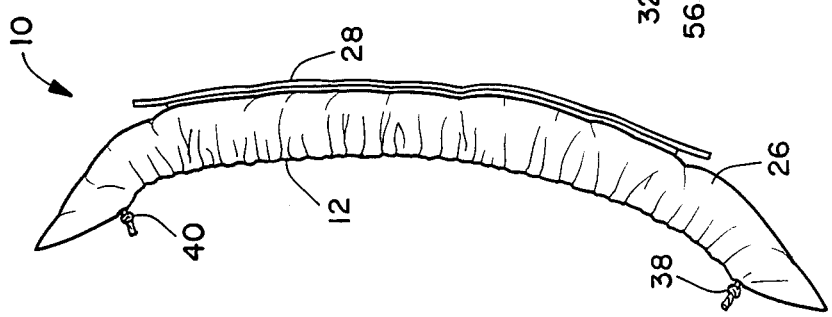
FIG. 4 is a side view of the pad in accordance with the invention.
Figure 3:
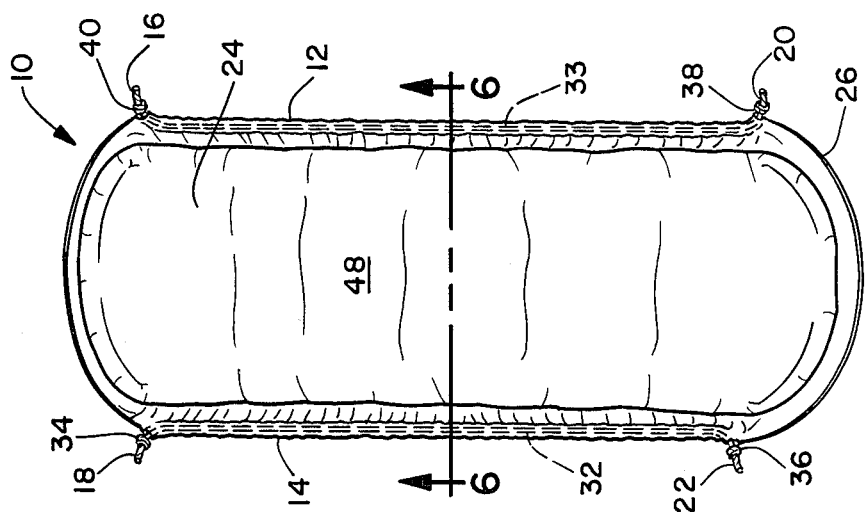
FIG. 3 is a plan view of a pad in accordance with the invention.

FIGS. 3, 4 and 5 are a plan view, side view and end view of pad 10 formed in accordance with the invention. The pad is provided with upstanding side walls 12. The pad further is maintained in a curved shape as the strings 32 and 33 are somewhat shorter than the length of backing member 26. The peel strip 28 extends substantially the full length of the pad. The absorbent pad rests in the bottom of the trough formed by the backing member 26 that is shortened by the upstanding sides 14 and 12 that contain the draw strings. The cross-section of FIG. 6 shows the permeable cover member 48 over absorbent 50. The absorbent 50 is shown as adhered to the impermeable backing member 26 by lines of construction adhesive 44. Garment attachment adhesive 51 is protected prior to use by the peel strip 28 that is removed prior to adhering the garment to the underwear of the wearer. The adjustment strings 32 and 33 are free to move within the channels 54 and 56.

Figure 7:
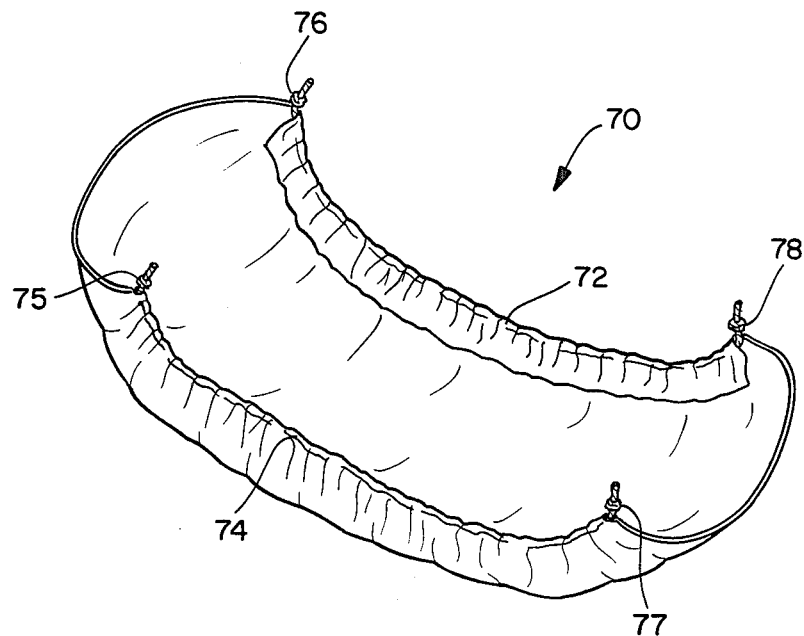
FIG. 7 is a view of a separate backing member and disposal means for feminine pads.
Figure 8:
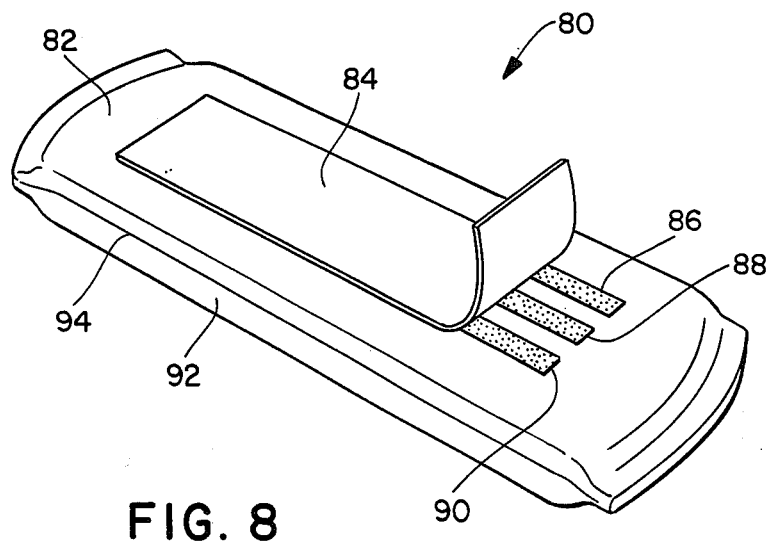
FIG. 8 is a view of a feminine pad suitable for use with the backing member of FIG. 7.
Figure 9:
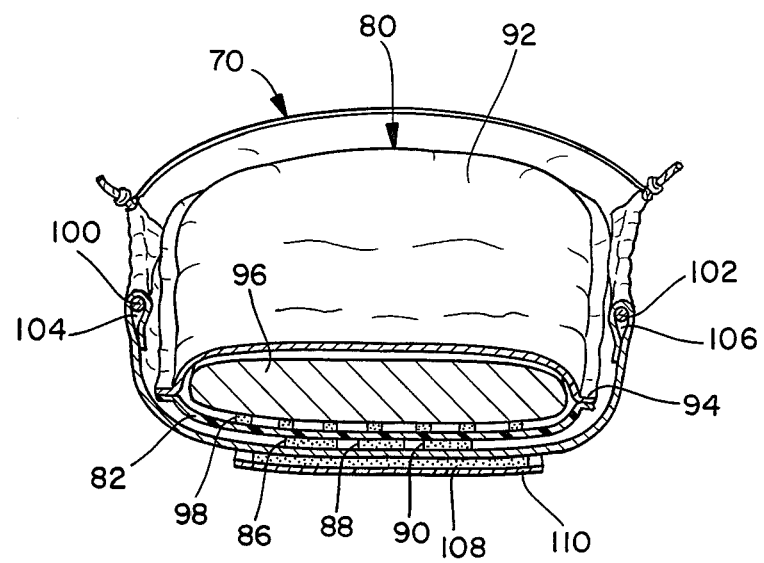
FIG. 9 is a cross-sectional view of the member such as in FIG. 7 with a pad such as in FIG. 8 in place.

An alternative form of the invention is illustrated in FIGS. 7, 8 and 9. FIG. 7 illustrates an impermeable holder 70 shaped into a curved configuration by draw strings located in channels 72 and 74 at its edges. The draw strings may be adjusted by pulling at the ends of the strings 75, 76, 77 and 78. The impermeable-shaped member 70 may be formed out of any suitable material such as a plastic film or a laminated plastic film with a cloth-like material. Into the impermeable backing member 70 may be placed a pressure sensitive adhesive-backed absorbent pad 80 such as shown in FIG. 8. The pad 80 may be formed of any conventional absorbent pad structure having a pressure sensitive garment attachment adhesive. As shown, pad 80 has an impermeable backing member 82 has adhered thereto a paper peel strip 84 that is placed over three lines of adhesive 86, 88 and 90. The pad 80 is provided with a permeable cover material 92 that is joined to the impermeable backing 82 at seal line 94.

FIG. 9 is a cross-section of the pad 80 placed in the impermeable holder member 70 after removal of peel strip 84. The absorbent 96 is adhered to the impermeable backing member of the pad 80 by lines of construction adhesive 98. Draw strings 100 and 102 are free to move within channels 104 and 106. The impermeable-shaped holder 70 is provided as shown with a garment-attachment adhesive 108 protected by peel strip 110. As can be seen by the cross-sectional view of FIG. 9, the pad resting within the impermeable-shaped member provides a shaped protection with a double baffle arrangement to prevent leakage. It allows the use of an unshaped pad 80 that is molded to the curved shape of the holder member 70. The pad holder 70 further provides a disposal means as the used pad and holder may be rolled with the garment attachment adhesive 108 sealing the roll. Leakage is minimized as both the baffle 82 of the pad and the impermeable holder member 70 prevent leakage. This construction gives the wearer of the pad the option of utilizing the device 70 on heavy flow days when leakage may be a problem or during the nighttime, but using the pad 80 without the holder member 70 at times of lighter flow.

Figure 10:
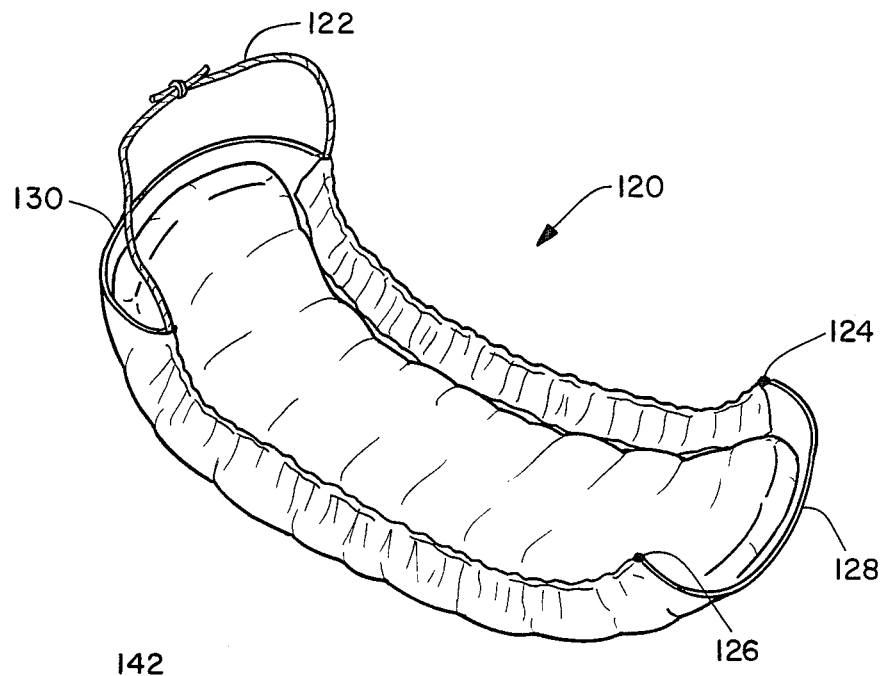
FIG. 10 and FIG. 11 are alternate draw string arrangements for pads in accordance with the invention.
Figure 11:
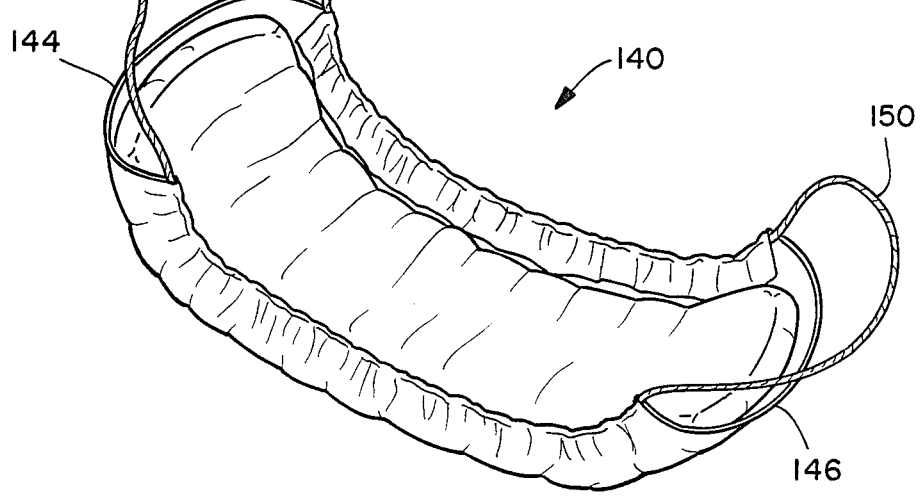

FIG. 10 illustrates an alternate arrangement of a pad 120 in which the draw string is only adjustable from one end. The draw string 122 is permanently fastened at 124 and 126. The string 122 may be pulled after pad 120 is rolled from end 128 to end 130 to form either a carrying package prior to use or for disposal after use. This structure may have an advantage in formation in that the strings are less likely to enter the channels and cause the garment to lose its shape and also the strings would then not be available to be pulled to hold the sides of the rolled pad. FIG. 11 is a variation in which a single string is used that is joined in a loop through the edges of pad 140 and knotted at 142. This pad may be rolled from either end 144 or end 146 with adjustment either of loop 148 or 150 to draw the sides of the rolled pad in to hold the roll either prior to use or for disposal after use.

Figure 12:
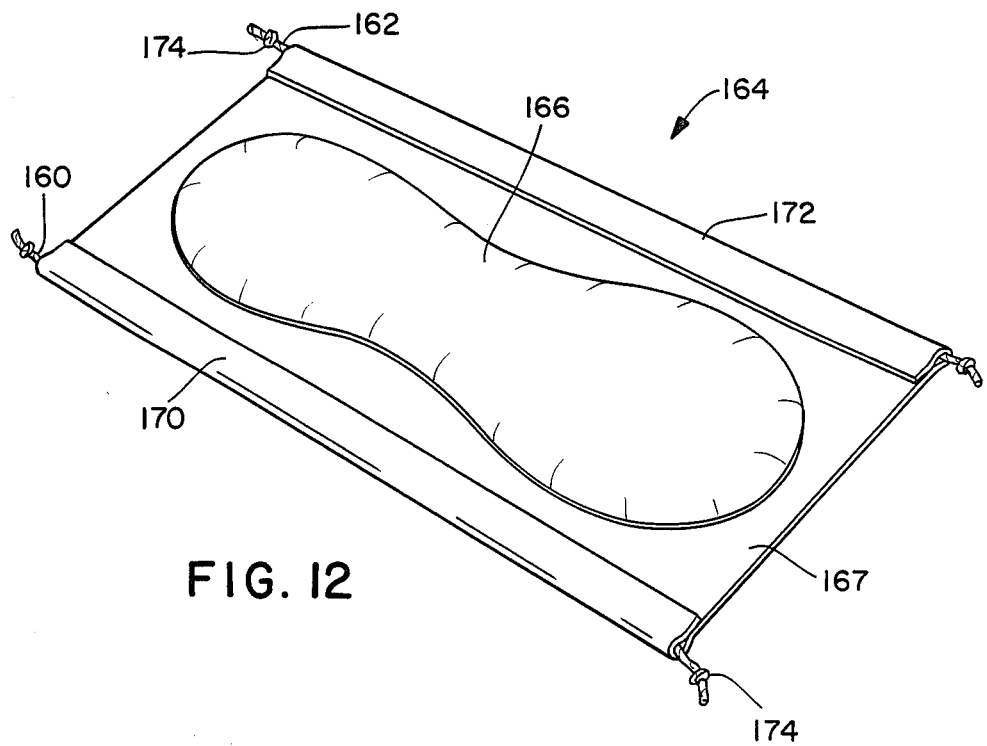
FIG. 12 is an alternate absorptive pad in accordance with the invention.

In the alternate embodiment shown in FIG. 12, the draw strings 160 and 162 of feminine napkin 164 are longer than the liquid-impermeable backing member 167. Pad 164 is provided with an absorbent section 166. In the embodiment of FIG. 12 the draw strings do not serve the purpose of shaping the pad but are available to serve the purpose of holding the rolled pad in a roll and protecting the sides of the pad, both prior to use and also when the pad is rolled after use for disposal. The pad 164 is provided with edge channels 170 and 172 in which strings 160 and 162 move freely. The strings are provided with knots 174 or other means at the ends of the strings to keep the strings from being withdrawn into the channels 170 and 172.

The material forming the draw string backing member may be any liquid-impermeable member that has sufficient strength to form the channels for the adjustment strings. Typical of such materials are polymer films of polypropylene or polyethylene. Also suitable are laminates of films and fabric materials. A preferred material is a laminate of spunbonded material and a polymer film such as polypropylene or ethyl methacrylate-polypropylene copolymer. It is preferred that the outer surface of the draw string backing member be a fabric, as this is more comfortable to the wearer. The backing material, while indicated as liquid impermeable, may be permeable to gases. Further, in the instance of the draw string holder device that may be utilized with a conventional adhesive-backed pad, the material would not necessarily have to be impermeable as the pads are ordinarily provided with an impermeable backing.

The construction of the absorbent member of the pads of the invention may be any conventional absorbent utilized in feminine pad or incontinent garment construction. Typical of such materials are foams and meltblown absorbent materials. Preferred are wood fluff and coform, which is an air-formed blend of meltblown polypropylene and devilicated wood fibers as these materials are low in cost and have high absorbency.

The liquid-permeable cover material utilized in the pads of the invention may be any material that will be comfortable to the wearer and pass fluids to the absorbent. Typical of such materials are tissue and perforated films. Preferred are polypropylene spunbonded materials as these materials are low in cost and effective in passing liquids.

The construction of pads in accordance with the invention would be by conventional techniques with laydown of construction adhesives onto the liquid impermeable backing material; then application of a preformed pad of fluff absorbent and covering with a permeable member that may be adhesively or ultrasonically sealed to the backing member around the absorbent. The folding of the edges of the backing member to form channels for the draw strings and the knotting of the draw strings may be formed by conventional equipment.

The term draw strings is intended in this invention to include any movable adjustment member that may be located in channels at the edge of the pad. The adjustment members may be string, polymer strips, polymer cord either of a single large thread or formed of a multiplicity of filaments of the polymer. Further, the string may be formed of natural fibers such as cotton or other fibers used in forming string such as nylon, polyester or polypropylene. Blends of natural fibers such as cotton or manila fibers also could be used in combination with artificial fibers such as polypropylene. An elastic string may also be utilized to form a pad with sides that are able to resiliently hold their shape and prevent leakage.

The length of the strings may be adjusted to produce the desired curving and shortening of the pad. Generally, for a feminine pad, the shortening is such that the strings are between about 25 and about 45 percent shorter than the backing member to create a curved pad with raised sides. Further, the strings may be formed of elastic cord that will aid in the pad adjusting to the body as it is worn and movement of the wearer takes place. While it is preferred that the part of the pad in which the string is placed be straight for ease of formation, it is also possible that the pad could be hourglass shaped as is known in the formation of feminine pads.

The lateral flap at the edge between the longitudinal edge of the pad and the draw string generally extends between about ½ and about 1 inch beyond the absorbent in order to have an edge that extends about ¼ inch above the pad top, as is preferred for best fit and protection from leakage. Length of the pad may be formed for the desired use. It is known that pads for light flow are shorter and less absorbent than those pads for maximum flow.

The sealing of the rolled pad prior to use may be by any desired means. The sealing may be by exposing a portion of the garment adhesive. Further, a separate seal, such as shown in FIG. 2, may be utilized. Also, it is possible that the tightening of the adjustment strings at the edges will be sufficient to seal the pad without further sealing at the exposed end of the roll. Thin pads of about ¼ inch thickness are more easily held only by the strings, while thicker pads of about one-half inch or greater are more likely to require adhesive to hold their rolled pad.

The above description and drawings are intended to be representative rather than exhaustive of the invention. For instance, it is possible that the pad absorbent may be shaped in an hourglass shape while the backing member is rectangular as shown. In another variation, it is possible that the pad could be formed of two backing sheets that are sealed around the string to form a channel for the string rather than the folded edge channel as is illustrated. Also, while illustrated as suitable for feminine napkins and mild urinary incontinence, pads of the invention in larger sizes also could be used as infant diapers or as large adult incontinent garments. These and other variations are intended to be included by this invention that is intended to be only limited by the breadth of the claims attached hereto.

We claim:

1. A device for absorption of bodily exudate comprising an absorbent pad adhered to a flexible liquid impermeable backing material wherein said impermeable backing material extends beyond the longitudinal edges of said pad, forming flaps and wherein said flaps are provided with channels containing draw strings.

2. The device of claim 1 wherein said channels are generally parallel.

3. The device of claim 1 wherein said device is rolled with said channels on the ends of the roll.

4. The device of claim 1 wherein said strings are shorter than said channels, causing said pad to bend.

5. The device of claim 1 wherein said device is a feminine pad.

6. The device of claim 1 wherein said flaps extend upward toward the bodyside of the said pad to at least about the height of said absorbent.

7. The device of claim 3 wherein said roll is held to prevent unrolling prior to use by a seal of the surface of said roll.

8. The device of claim 7 wherein said roll has the strings in the channels pulled to cause said flaps to shorten and cover the ends of said roll.

9. The device of claim 1 wherein said backing material is provided with a fabric on its outer surface.

10. The device of claim 6 wherein said flaps extend about ¼ inch above the pad top.

11. The device of claim 1 wherein said draw strings are selected from the group formed from materials consisting of cotton, nylon polypropylene, polyester and combinations thereof.

12. The device of claim 1 wherein said strings are elastic.

13. The device of claim 1 wherein said draw strings are about 25–45 percent shorter than said channels.

14. A device for holding means for absorption of body exudate comprising a generally rectangular liquid impermeable web of material provided with draw strings in channels on the longitudinal edges of said web, wherein said web is provided with a strip of pressure sensitive adhesive and wherein said draw strings are shorter than said channels.

15. The device of claim 14 wherein said draw strings are about 25–45 percent shorter than said channels.

16. The device of claim 14 wherein an absorbent pad is adhesively adhered thereto.

17. The device of claim 14 wherein said draw strings are elastic.

18. A method of using feminine protection comprising providing a rolled feminine pad comprising an absorbent pad adhered to a flexible liquid impermeable backing material wherein said impermeable backing material extends beyond the longitudinal edges of said pad forming flaps and wherein said flaps are provided with channels containing draw strings, unrolling said pad, adhering said pad to the undergarment of the wearer, using said pad, removing said pad, rolling said pad, pulling said draw strings to tighten said flaps and cover the ends of said roll and maintain said pad in a roll and disposing of said pad.

* * * * *